(12) United States Patent
Bourel et al.

(10) Patent No.: US 6,932,969 B1
(45) Date of Patent: Aug. 23, 2005

(54) IG FRACTIONS HAVING IMMUNOMODULATORY ACTIVITY

(75) Inventors: Dominique Bourel, La Madeleine (FR); Martine Bruley-Rosset, La Varenne (FR); Frédéric Dhainaut, Boissy le Sec (FR); Jacky Lirochon, Breuillet (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 177 days.

(21) Appl. No.: 09/980,833

(22) PCT Filed: Jun. 7, 2000

(86) PCT No.: PCT/FR00/01560

§ 371 (c)(1),
(2), (4) Date: Feb. 12, 2002

(87) PCT Pub. No.: WO00/74717

PCT Pub. Date: Dec. 14, 2000

(30) Foreign Application Priority Data

Jun. 7, 1999 (FR) .................................. 99 07153
Dec. 29, 1999 (FR) .................................. 99 16632

(51) Int. Cl.[7] ...................... A61K 39/395; C07K 1/22; C07K 16/42

(52) U.S. Cl. ............................. 424/131.1; 424/158.1; 424/175.1; 424/810; 435/7.24; 435/7.95; 435/965; 436/822; 436/824; 530/387.2; 530/389.3; 530/389.8; 530/868

(58) Field of Search .................. 530/387.2, 389.3, 530/389.8, 4.3, 868; 424/158.1, 175.1, 810, 424/131.1; 435/5–6, 7.24, 7.32, 7.93, 7.95, 435/965; 436/506, 547, 822, 824

(56) References Cited

OTHER PUBLICATIONS

Berneman et al, Molecular Immunology, 30, 1499-1510, 1993.*
Franek et al, Molecular Immunology, 16, 389-394, 1979.*
Kimball, Introduction to Immunology, MacMillan Publishing Co. Inc., p. 10, 1983.*
Dietrich et al., "A V region-connected autoreactive of normal human serum immunoglobulin G,"*European Journal of Immunology* 22(7), pp. 1701-1706 (Jul. 1992).
Jordan et al., "Posttransplant therapy using high-does human Immunoglobulin (intravenous gammaglobulin) to control acute humoral rejection in renal and cardiac allograft recipients and potential mechanism of action,"*Transplantation* 66(6), pp. 800-805 (Sep. 1998).
Pacheco-Garcia et al "Altered pattern of connectivity in serum immunoglubulins from pemphigus vulgaris patients," *Scandinavian Journal of Immunology* 49(4), pp. 424-430 (Apr. 1999).
Flan, B. "Fractionation technique and biochemical properties of IV Ig! Technique de Fractionnement et Properties Biochimiques des Immunoglobulines Intraveineuses (IGIV),"*Sang Thrombose Vaisseaux* 11/Spec. Iss. (45-51), (Oct. 1999).

* cited by examiner

Primary Examiner—David Saunders
(74) Attorney, Agent, or Firm—Foley & Lardner LLP

(57) ABSTRACT

The invention concerns a method for preparing Ig fractions from human polyvalent intravenous Immunoglobulins (IV Ig) which are in particular likely to be responsible for the immunomodulatory effect observed during the treatment of certain autoimmune diseases. The invention concerns Ig fractions having reactivity to IgM, IgG F(ab')2 or DNP hapten and no or little reactivity to non-self antigens, that is Ig fractions which have idiotypic interactions among themselves (connected fraction) or which include natural antibodies reacting with the DNP hapten. Said fractions exhibit a polyreactivity to specific autoantigens.

13 Claims, 11 Drawing Sheets

IG FRACTIONS HAVING IMMUNOMODULATORY ACTIVITY

Figure 1A:
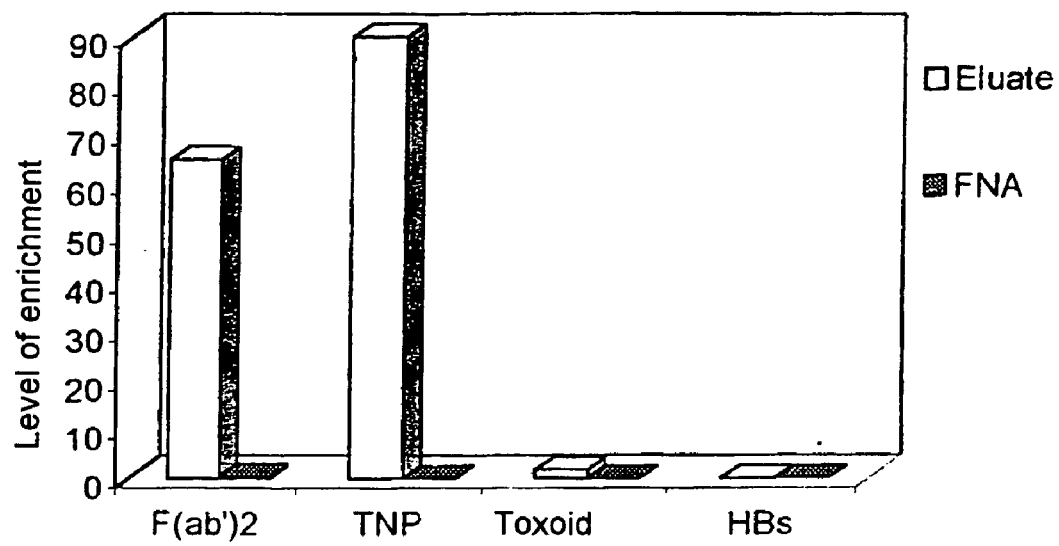

The present invention relates to a method for preparing Ig fractions from human polyvalent intravenous immunoglobulins (IVIgs) which are thought to be more particularly responsible for the immunomudulatory effect observed during treatments for certain autoimmune diseases. The invention relates to Ig fractions which have reactivity with respect to IgMs, IgG F(ab')2s or the hapten DNP, and little or no reactivity with respect to non-self antigens, i.e. fractions of Igs which exhibit interactions of the idiotypic type with one another (connected fraction) or which comprise natural antibodies which react with the hapten DNP. These fractions show polyreactivity with respect to given autoantigens.

IVIg preparations have been used for many years for treating multiple pathological conditions. The major indications may be grouped into three therapeutic targets:
primary or secondary immune deficiencies,
treatment of certain autoimmune diseases,
infectious complications and graft-versus-host disease after allogenic hematopoietic cell transplants.

In the case of immune deficiencies, IVIgs constitute a substitutive treatment which makes it possible to provide IGgs, the plasma concentration of which in patients is not sufficient to neutralize the development of viral or bacterial infections.

For autoimmune diseases, the effectiveness of IVIgs is related to complex immunomodulatory effects. IVIgs are prescribed in the context of bone marrow transplants, and correspond to a substitutive treatment while awaiting the immunological reconstitution of the individuals having received a transplant and exert an immunomodulatory effect with regard to graft-versus-host disease.

IVIgs are prepared from a pool of plasmas originating from several thousands of donors; they have a distribution of subclasses and antibody specificities reflecting that of the general population. Thus, IVIgs may be considered to be a product containing the entire repertoire of natural antibodies and of antibodies directed against outside antigens and autoantigens.

The concept of immunoregulation by IVIgs has been widely developed since the demonstration of their effectiveness in autoimmune thrombocytopenic purpura (AITP) in 1981 (1). IVIgs have subsequently been used in many autoimmune or inflammatory pathological conditions. Some indications, for which the effectiveness of IVIgs has been clearly established, are officially recognized by the regulating authorities. They are AITP, Kawasaki disease, in which they very effectively prevent complications concerning aneurysms (2, 3), allogenic hematopoietic cell trans-plantation, in which they modulate the graft-versus-host reaction (4) and, more recently, Birdshot retinochoroiditis, in which they improve visual acuity and in which they sometimes enable corticotherapy to be reduced (5).

Other indications are considered by experts to be justified; some cytopenias, for example, in which IVIgs lead to rapid but often transient improvement (6), and in hemophilias with inhibitors (anti-factor VIII autoantibodies), in which, on the other hand, the improvement may be long-lasting (7, 8). Contradictory results have been obtained in recurrent abortions, with encouraging success rates in certain series (9, 10).

For about ten years, there has been a very significant rapid development of IVIgs in neurology by virtue of controlled multicenter studies with both quantitative (neurological scores) and qualitative (number of patients improved) effectiveness criteria. Thus, in adult Guillain-Barré syndrome, IVIgs are as effective as plasma exchanges and are tolerated better (11, 12). They are recommended as first line treatment in pediatric forms (13). They are more effective versus placebo in chronic inflammatory demyelinating poly-neuropathies (14) and in dermatomyositis (15). They are as effective as and better tolerated than plasma exchanges in acute episodes of myasthenia (16). Finally, a study versus placebo has demonstrated the effectiveness of IVIgs in relapsing/remitting forms of multiple sclerosis (17).

Several mechanisms have been proposed to explain the diversity of action of IVIgs (18):
blocking of Fc receptors at the surface of macro-phages, monocytes, neutrophils and eosinophils,
neutralization of circulating autoantibodies by anti-idiotype antibodies,
inhibition of the harmful effects due to complement activation,
modulation of the cytokine network,
and/or selection of immune repertoires by inter-action with T and B lymphocytes.

These mechanisms may account for both the early and prolonged effects of IVIgs.

An Ig fraction (termed connected fraction) may be purified on an affinity column in which IVIg F(ab')2s or whole IgGs have been coupled to Sepharose beads (19 and 20). The IgMs contained in the serum of normal individuals bind to the F(ab')2 fragments of the autologous IgGs and inhibit the association of these IgGs with autoantigens (21). IgMs contribute to regulating the natural autoreactivity of IgGs through interactions of the idiotypic type (21). These Igs, or their F(ab')2s, may inhibit the binding of certain autoantibodies to their antigens, as was demonstrated by tests carried out in vitro (22). The connected Ig fraction obtained from IVIgs would contain in particular antibodies which recognize anti-idiotypic determinants present on IgG or IgM autoantibodies capable of neutralizing one another and of modifying the function and dynamics of the idiotypic network (23). Moreover, an Ig fraction characterized in that it reacts with the hapten DNP is described as containing polyreactive and autoreactive natural antibodies (24).

Other documents describe the general principle for obtaining connected fractions. Among these documents, mention may be made of patent application WO 98/26086, which relates to a method for preparing a purified composition of antibodies comprising anti-idiotype antibodies, said method consisting in adsorbing a pool of IgGs onto a solid substrate containing an idiotypic determinant of an autoantibody, and in eluting.

EP 293 606 describes a general method for purifying an antibody X by idiotypic/anti-idiotypic interaction, comprising the following steps:
a) attaching an antibody Y to a solid support, said antibody recognizing the idiotype of X,
b) bringing a sample containing an antibody X into contact with the solid support in a suitable buffer,
c) eluting and d) recovering the purified antibody X.

WO 97/19113 relates to the use of monoclonal anti-idiotypic antibodies of the IgG type as immuno-regulators of the immune response, in particular for treating autoimmune diseases.

Currently, the tolerance and the effectiveness of the polyvalent IgGs made commercially available, in particular TEGELINE® (LFB, France), are in particular recognized in the treatment of ITP, of Kawasaki disease and of retinochoroiditis of the "Birdshot" type, these being pathological conditions for which marketing authorizations have been obtained. However, the current doses in these indications are considerable and the method of administration remains laborious and complex (infusions lasting several hours in a hospital environment). The problem therefore consists in preparing a fraction which is active in autoimmune pathological conditions, so as to make the preparation more effective and more convenient to use.

The objective which is the basis of the present invention is therefore to obtain specific Igs which allow doses to be decreased, which have the same or even increased effectiveness and better tolerance, and the method of administration of which is simpler. It has been shown that it is possible to prepare fractions which address the problems mentioned above by preparing them from pools of Igs such that they have anti-IgM, anti-Ig F(ab')2 or anti-DNP reactivity and little or no reactivity with respect to non-self antigens, and/or which show polyreactivity with respect to certain autoantigens.

DESCRIPTION

Thus, the present invention relates to the purification of the Igs contained in the polyvalent IVIgs which are thought to be more particularly responsible for the immunomodulatory effect observed during the treatment of certain autoimmune diseases. The invention is based on the characteristics of these IgG fractions which have reactivity with respect to IgMs, IgG F(ab')2s or the hapten DNP, and little or no reactivity with respect to the tetanus toxoid and the HBs antigen (non-self antigens), i.e. fractions comprising Igs exhibiting interactions of the idiotypic type with one another (connected fraction) or comprising natural antibodies. These fractions show polyreactivity with respect to certain autoantigens.

The Ig fractions are prepared by affinity chromatography using the property of these Igs of recognizing one another, of recognizing IgMs or of binding to the hapten DNP. The raw material used to obtain these fractions originates from polyvalent Igs, in particular those which are prepared and marketed by LFB (France), or from any other intermediate fraction obtained during the method for producing polyvalent IVIgs for therapeutic use. The general method for preparing polyvalent IVIgs essentially comprises the following steps:

fractionation of the plasma originating from a pool of donors by precipitation, adsorption and/or filtration and then ultrafiltration (production of a first fraction, "PSO 1"), treatment with pepsin at acid pH, formulation, distribution and lyophilization (production of the product TEGELINE®), another treatment may use anion exchange column chromatography, ultrafiltration, production of an intermediate fraction (named "PSO 2") and heating, ultrafiltration, formulation and distribution (production of a liquid IVIg fraction).

In the context of the invention, the term "polyvalent Igs" is intended to mean whole polyvalent IgGs or IgMs, polyvalent IgG fragments, such as F(ab')2 or F(ab), and any intermediate fraction obtained during the method for producing polyvalent IVIgs.

A first aspect of the invention relates to an Ig fraction which reacts with at least one component selected from IgMs, IgG F(ab')2s and the hapten DNP, with a level of enrichment of greater than 20 compared to the activity of the initial polyvalent Igs, and in that it does not react with the tetanus toxoid or the HBs antigen, with a level of enrichment of less than 5 compared to the activity of the initial polyvalent Igs.

This Ig fraction may consist of an IgG fraction or an IgM fraction.

Preferably, it reacts with a component selected from IgMs, IgG F(ab')2s and the hapten DNP, with a level of enrichment of greater than 40 compared to the activity of the initial polyvalent Igs.

The fraction according to the invention may also react with at least one of the autoantigens selected from myosin, actin, tubulin and myelin basic protein (MBP), with a level of enrichment of greater than 10, preferably 20, compared to the activity of the initial polyvalent Igs.

Advantageously, the fraction reacts with all of the autoantigens mentioned above.

A preferred fraction according to the invention may be defined in that it reacts with a component selected from IgMs, IgG F(ab')2s and the hapten DNP, with a level of enrichment of greater than 40 compared to the activity of the initial polyvalent Igs, and with myosin, actin, tubulin and MBP, with a mean level of enrichment of greater than 20 compared to the activity of the initial polyvalent Igs.

The fractions mentioned may react with IgMs or IgG F(ab')2s. They may also react with the hapten DNP and, in this case, they do not react with IgMs or IgG F(ab')2s.

A second aspect of the invention relates to a method for preparing Ig fractions, characterized in that it comprises the following steps:

a) preparing an insoluble support onto which is grafted a component selected from polyvalent IgGs, polyvalent IgMs and DNP-lysin, b) adsorbing polyvalent Igs onto the support obtained in step a), c) eluting the Igs retained on the portion of immunoglobulins bound to the support, so as to collect the fraction connected through IgG-IgG or IgM-IgG idiotypic interactions, or eluting the fraction which interacts with DNP, d) selecting the fractions having reactivity with respect to IgMs, IgG F(ab')2s or the hapten DNP, little or no reactivity with respect to non-self antigens and/or polyreactivity with respect to given autoantigens, e) selecting the fractions having activity which inhibits the proliferation of lymphocytes in mixed culture, preferably with an effectiveness 10 to 50 times greater than TEGELINE®.

In this method, the Igs absorbed may be IgGs or IgMs.

The Ig fractions obtained are prepared from polyvalent Igs or any other intermediate fraction obtained during the method for producing IVIgs for therapeutic use. These polyvalent Igs may be IgGs or IgMs.

Within the polyvalent Igs, there are natural antibodies which interact with the hapten DNP and antibodies which interact with the idiotypes expressed by autoantibodies of the IgG or IgM type (connected fraction) and which have a certain autoreactivity. In the context of the invention, the term "connected fraction" is intended to mean a fraction which has a high percentage of Igs which interact with one another or with IgGs or IgMs via idiotype-anti-idiotype binding.

The strategy used to determine, among the various fractions, the fraction(s) having the desired properties, i.e. the fractions which contain the highest autoreactivity titer and which react with the greatest number of autoantigens, consists in subjecting them to screening possibly comprising several successive steps.

The various in vitro and/or in vivo assays used make it possible to select, at each step, the most active fractions according to increasingly specific criteria.

The method according to the invention may therefore comprise steps for selecting Ig fractions having given characteristics.

In this sense, step d) may comprise measuring the level of enrichment of antibodies reactive against IgMs, IgG F(ab')2s or the hapten DNP used for the purification.

Step d) may also comprise measuring the reactivity for the tetanus toxoid and the HBs antigen, taking the level of enrichment as a control value.

Preferably, step d) comprises an ELISA assay carried out on a panel of autoantigens selected in particular from actin, myosin, MBP and tubulin.

Step d) of the method according to the invention may also comprise a competition assay in order to control the neutralizing activity of the fractions with respect to autoantibodies originating from serum of patients suffering from autoimmune diseases, and/or an assay of inhibition of the mixed lymphocyte reaction with human cells in order to measure the inhibitory capacity.

This mixed lymphocyte reaction assay may comprise the following steps:
- taking blood samples from a donor A and from a donor B who are incompatible in terms of major histocompatibility complex (MHC) antigens,
- purifying the mononuclear cells on ficoll,
- culturing $2 \times 10^5$ cells from donor B in the presence of $210^5$ cells from donor A,
- measuring the proliferation of the cells on day 4 by measuring tritiated thymidine incorporation.

Step a) consists in grafting polyvalent IgGs, polyvalent IgMs or DNP-Lysine onto an insoluble support, in particular onto a Sepharose®, Trisacryl®, Affiprep® or Affigel® gel, or gels activated with the groups CNBr, NHS or $C_5H_8O_2$ (glutaraldehyde). The Igs deposited onto the solid support obtained in step a) are adsorbed either in the form of polyvalent Igs lyophilized and redissolved or in liquid form, or in the form of intermediate fractions obtained during a method for producing polyvalent Igs. The Igs deposited comprise IgGs or IgMs.

Advantageously, the absorption is carried out under temperature conditions ranging from 4° to 40° C. and in a 20 mM phosphate buffer or equivalent comprising NaCl, the concentration of which may range from 0 M to 3 M.

The Igs retained in step b) are preferably eluted in step c) with a buffer containing ions which dissociate Ag-Ab or DNP-Ab binding, selected in particular from chaotropes such as glycine-HCl or sodium iodide (NaI), under conditions which vary the pH, preferably between 2.8 and 4.0.

In a particular embodiment, this method comprises the following steps:
a) Grafting polyvalent IgGs, polyvalent IgMs or DNP-lysine onto a solid support or affinity (immunoadsorbant) support conventionally used in affinity chromatography. Such supports are well known to those skilled in the art. Mention may be made, for example, of a Sepharose®, Trisacryl®, Affiprep® or Affigel® gel, or gels activated with the groups CNBr, NHS or $C_5H_8O_2$ (glutaraldehyde).
b) Adsorbing Igs in 20 mM phosphate buffer or equivalent comprising NaCl, the concentration of which may range from 0 M to 3 M, onto the solid support obtained in step a), deposited either in the form of polyvalent Igs lyophilized and redissolved or in liquid form, or in the form of intermediate fractions obtained during the method for producing polyvalent Igs. The Igs adsorbed comprise IgGs or IgMs.
c) Eluting the Igs retained in step b) with a buffer containing ions which dissociate Ag-Ac binding, selected in particular from chaotropes such as glycine-HCl or sodium iodide (NaI), under conditions which vary the pH, preferably between 2.8 and 4.0, and/or the ionic strength, and/or by any other equivalent method for breaking IgG-IgG, IgG-IgM or Ig-DNP-Lysine binding, so as to obtain Ig fractions having a reactivity profile which is different from that of the starting polyvalent Igs.
d) Measuring, by ELISA, the level of enrichment of antibodies reactive against IgMs, IgG F(ab')2s or the hapten DNP or TNP used for the purification, measuring the reactivity for the tetanus toxoid and the HBs antigen, taking the level of enrichment as a control value, and measuring the level of enrichment of reactivity with respect to a panel of autoantigens selected in particular from actin, myosin, MBP and tubulin.

As mentioned above, an additional step comprising a lymphocyte reaction assay may also be included in this method.

In each case, the fraction which is not retained on the various columns may also be used as a control in addition to the initial preparation of Ig.

Of course, certain parameters of the method may be modified at the convenience of those skilled in the art, by simple routine experiments. The invention therefore also relates to a method mentioned above, in which the parameters are determined as a function of the fractions which have been selected beforehand in step d). It involves defining the optimum parameters for obtaining a fraction having the particular properties desired and then applying these parameters on the scale of an industrial method according to the invention. Such parameters may be the parameters which characterize the fractions described above. Thus, the method may be suitable for obtaining the fractions described above. Similarly, the invention is directed toward a method for the industrial production of fractions having reactivity with respect to a component selected from IgMs, IgG F(ab')2s and the hapten DNP, little or no reactivity with respect to non-self antigens and polyreactivity with respect to given autoantigens, characterized in that steps a), b) and c) described above are carried out, respecting or adjusting the parameters used in preparing the fractions of interest selected beforehand.

The subject of the invention is also the fractions which can be obtained using the method mentioned above.

The immunomodulatory properties of the few fractions selected using the in vitro assays may also be determined in vivo in several animal models of autoimmune diseases and of graft-versus-host disease (GVH) after allografts.

Several types of model have been chosen, depending on the mechanism of action involved:
- models in which the effector function is carried out via T cells or by antibodies,
- models in which the mechanisms depend on interaction with F(ab')2s or Fcs.

Two experimental autoimmune diseases in rats, in which the effector function is carried out via T cells, are more particularly chosen since they have been described as being sensitive to the administration of IVIgs and have the advantage of being able to provide a rapid response regarding the effectiveness of the fractions (the protective effects can be evaluated in approximately 4 weeks). They are the following models:

1) experimental autoimmune uveitis, or EAU, induced by injecting the bovine retinal antigen, or the immunodominant peptide thereof, into Lewis rats.

2) Rheumatoid arthritis (RA) induced in Dark Agouti rats by injecting bovine type II collagen.

In each case, the severity of the disease is evaluated clinically and/or histopathologically and several biological parameters, such as weight loss, production of antibodies against the autoantigen injected, are measured over time.

A model of acute GVH in rats was added since this disease has been described as being sensitive to the administration of IVIgs. GVH is induced in hybrid rats (Lewis×Brown-Norway) by injecting lymphoid cells originating from Lewis rats. The disease is evaluated by weight loss, presence of erythema and rate of mortality.

The autoimmune hemolytic anemia (AHA) animal model, which mainly involves the action of antibodies, is close to the hemolytic pathological conditions observed in humans. It is induced by injecting rat red blood cells (RBCs) into C3H mice having previously undergone a splenectomy. This assay is useful because of the effectiveness of IVIgs observed in hemolytic anemia in humans. The development of anemia is monitored via the decrease in the number of RBCs and the appearance in the serum of the animals of autoantibodies directed against their own RBCs.

The protective effect of the product TEGELINE®, polyvalent IgGs, polyvalent IgMs or any other inter-mediate product obtained during the method for producing polyvalent Igs is assayed beforehand in the models and the optimum conditions for administration (dose, number, interval and route of injection) are determined. The fractions selected are injected at doses five to twenty times lower than those for TEGELINE®, and the effectiveness of these treatments is measured in the various models of autoimmune diseases.

In addition, experimental models using human cells may be used.

The humanized SCID/NOD mouse appears to be the best model for evaluating the effectiveness in vivo on pathological human cells of the fractions preselected using the assays on animal models.

The models of primary biliary cirrhosis, of myasthenia and of Hashimoto's thyroiditis were selected since the cells originating from these pathological conditions have already been successfully transplanted into SCID mice. Other pathological conditions may subsequently be chosen.

In a subsequent phase, and with the aim of increasing knowledge regarding the mechanism of action of a given fraction, which has been demonstrated as being effective, other complementary models may be used in order to extend the indications for use of the IVIg-derived fractions, such as TEGELINE® or others.

Step d) may therefore also comprise one or more in vitro assay or assays, in particular the assays described above.

Thus, the method according to the invention in particular allows the preparation and selection of the fractions having the characteristics defined above.

Once the fractions of interest have been identified, the parameters of steps a), b) and c) may be employed in the context of an industrial method for producing said fractions. Such a method with the suitable parameters according to the fractions of interest selected beforehand is an additional subject of the invention.

A complementary aspect of the invention relates to the fractions which can be obtained using the method defined above.

It should be noted that the description of the present invention is not limiting, and that equivalent methods and equivalent fractions also make up the invention.

The fractions according to the invention have several advantages, the main ones of which are as follows:

A decrease in the doses. Given that the novel product provided corresponds to a fraction contained in polyvalent Igs, the amount of Ig having immunomodulatory properties which is injected is less than that of the IVIgs conventionally prescribed. The effective doses may be reduced by a factor of 5 to 20, or even more. This is a considerable advantage since the doses currently used for the available polyvalent Igs are very high: of the order of 1 to 2 g/kg.

An effectiveness which is maintained or even increased since the product is enriched in immuno-modulatory Igs.

Better tolerance. With lower concentrations, the tolerance of the novel product is improved. Specifically, it is currently necessary to take certain precautions when administering IVIgs with, in particular, slow infusion of the product over several hours in order to avoid certain side effects, such as for example allergic reactions.

Simplified prescription. The administration of low doses makes it possible to instigate ambulatory treatments which substitute for the current infusions carried out in a hospital environment.

An additional aspect relates to the use of the Ig fractions according to invention, for preparing a medicinal product. This medicinal product is more particularly suitable for treating autoimmune diseases, GVH, and/or graft rejection after transplantation.

The fractions according to the invention are useful for preparing a medicinal product intended for the treatment of Kawasaki disease and/or of Birdshot retinochoroiditis, optionally in combination with corticotherapy, and/or for the treatment of certain cytopenias and/or of hemophilias with inhibitors (anti-factor VIII autoantibodies), and/or for preventing or impeding immune rejection of cell and/or organ transplants and the development of GVH after transplantation of allogenic cells.

The fractions according to the invention are also useful for preparing a medicinal product intended for the treatment of neurological diseases, in particular adult Guillain-Barré syndrome, chronic demyelinating inflammatory polyneuropathies, dermatomyositis, myasthenia and/or multiple sclerosis.

For the remainder of the description, reference will be made to the legends of the figures given hereinafter.

LEGENDS

FIGS. 1A–1D: Evaluation of the properties of a fraction obtained using TEGELINE® (solid support based on Affigel grafted with TEGELINE®).

The parameters of the method for preparing this fraction are explained in greater detail in Example 1 hereinafter.

FNA means fraction not absorbed.

Figure 1B:
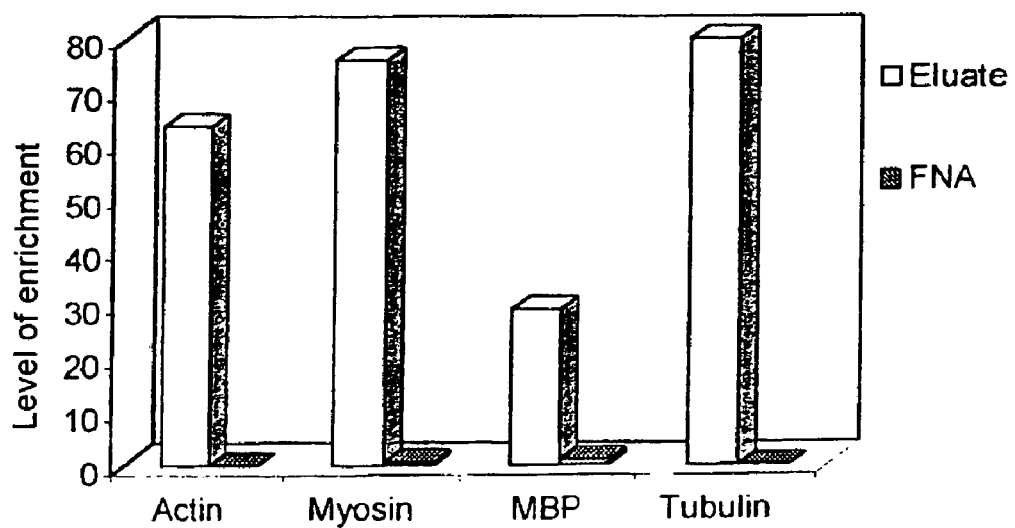
Figure 1C:
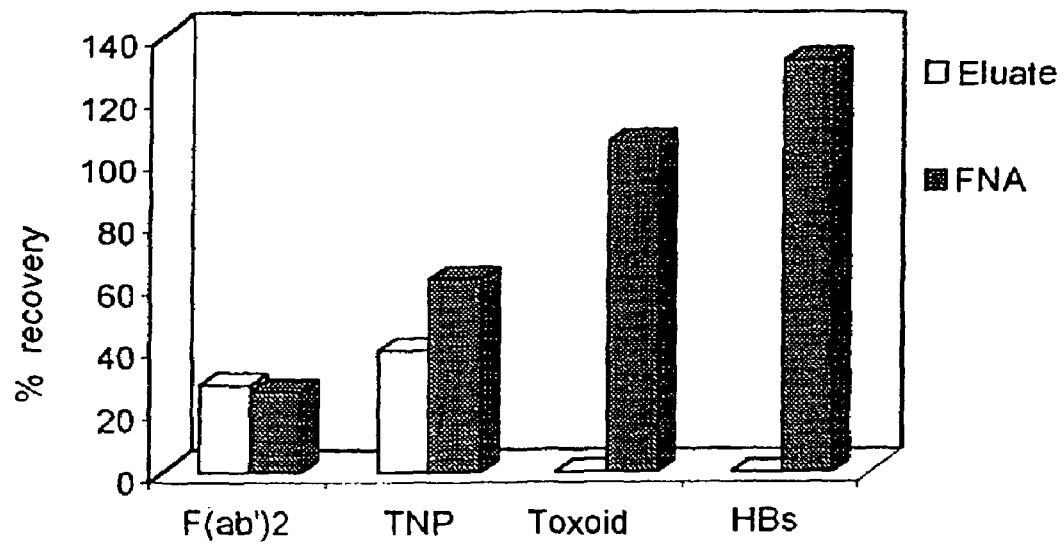
Figure 1D:
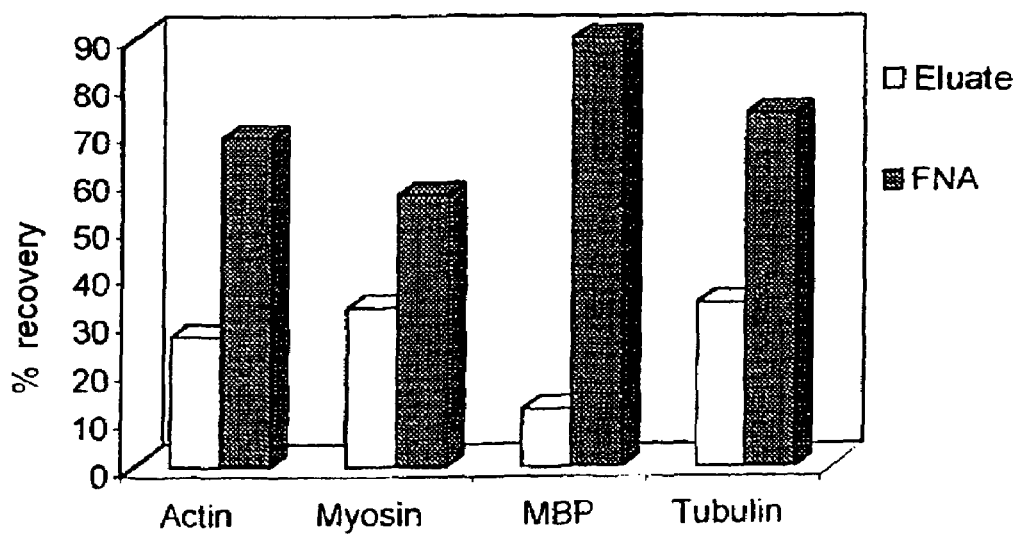

FIGS. 1A and 1C illustrate the specific reactivity with respect to IgG F(ab')2s and FIGS. 1B and 1D represent the reactivity with respect to autoantigens.

FIGS. 2A–2D: Evaluation of the properties for a fraction obtained using TEGELINE® (solid support based on NHS-Sepharose).

The parameters of the method for preparing this fraction are explained in greater detail in Example 2 hereinafter.

Figure 2A:
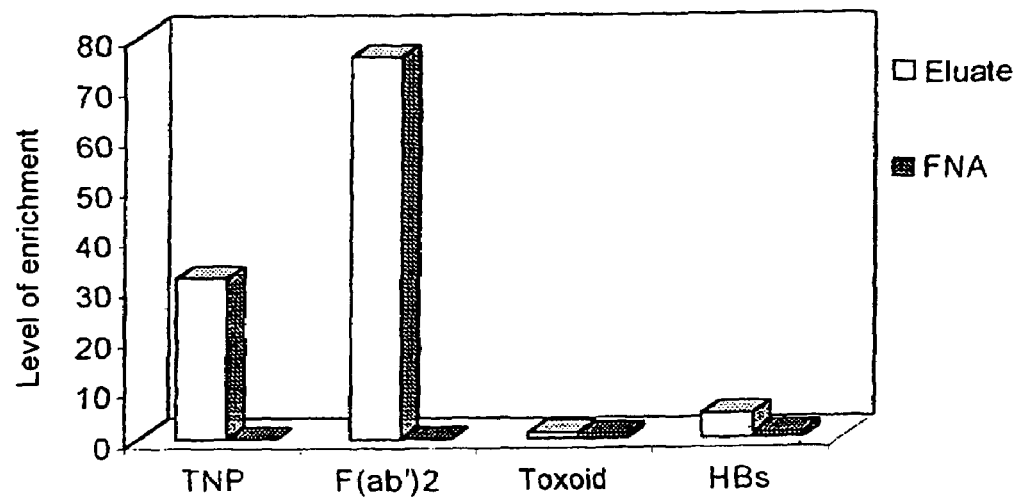
Figure 2B:
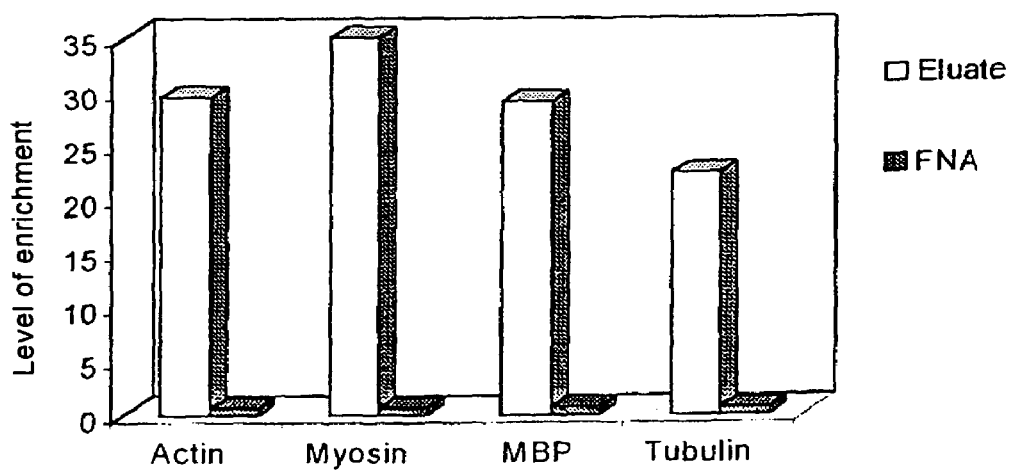
Figure 2C:
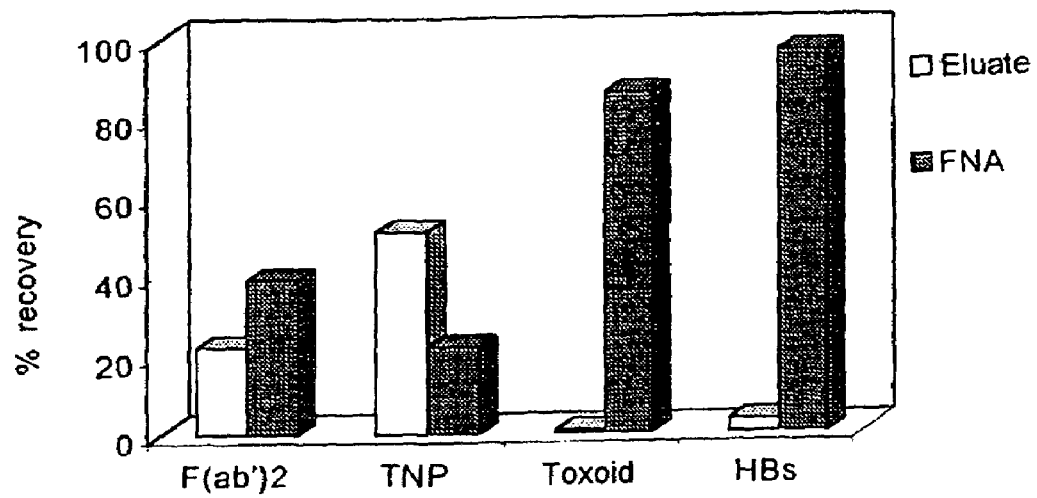
Figure 2D:
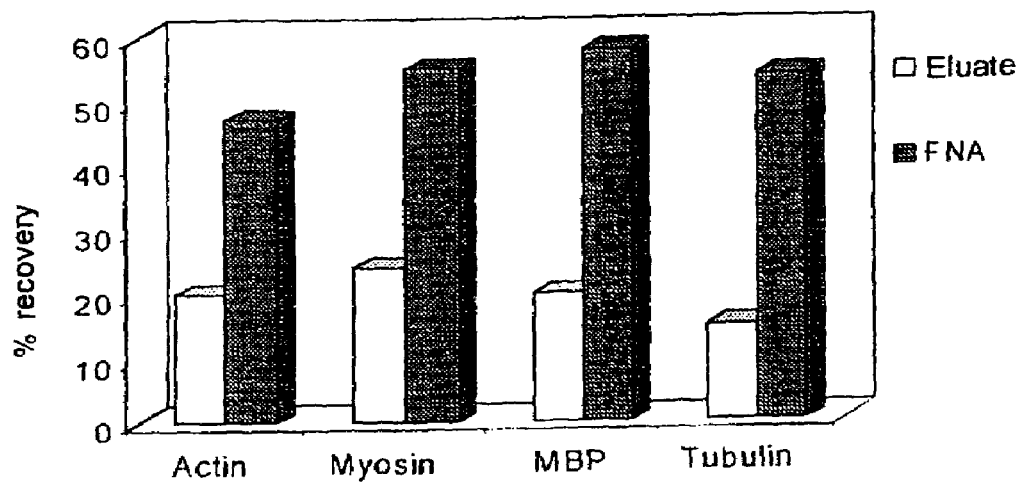

FIGS. 2A and 2C illustrate the specific reactivity with respect to IgG F(ab')2s and FIGS. 2B and 2D represent the reactivity with respect to autoantigens.

FIGS. 3A–3D: Evaluation of the properties of a fraction obtained using TEGELINE® (solid support based on NHS-AffiPrep with DNP-Lysine).

The parameters of the method for preparing this fraction are explained in greater detail in Example 3 hereinafter.

Figure 3A:
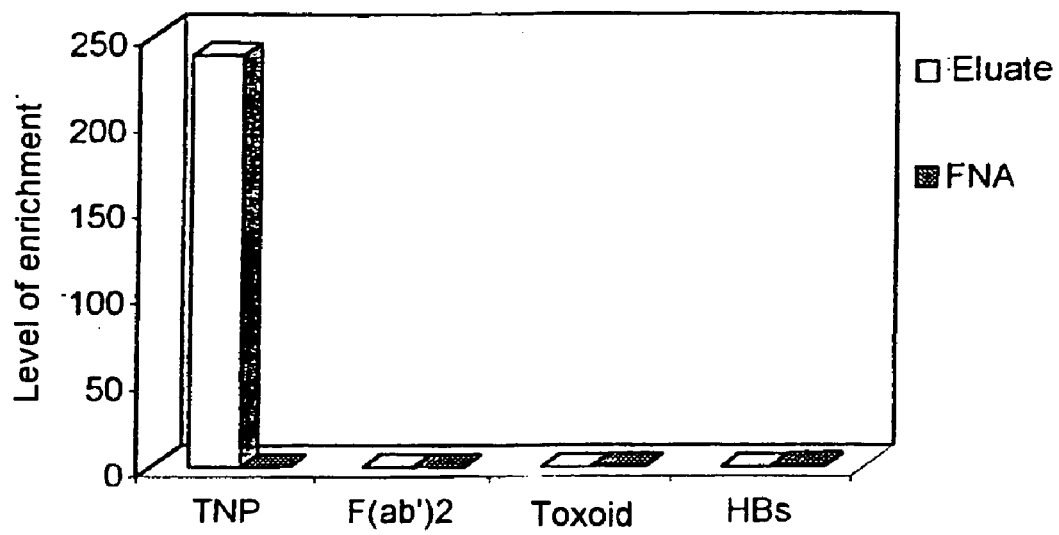
Figure 3B:
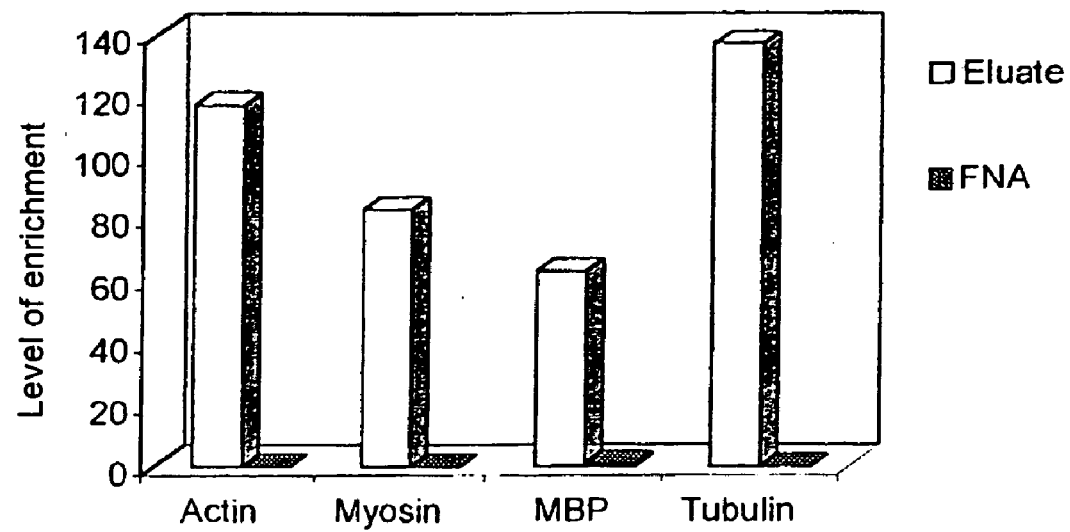
Figure 3C:
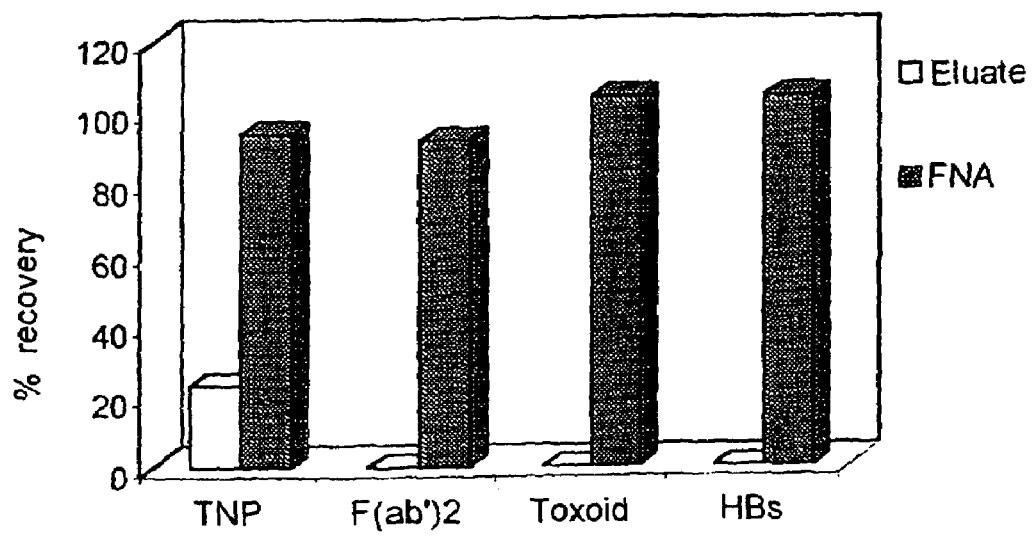
Figure 3D:
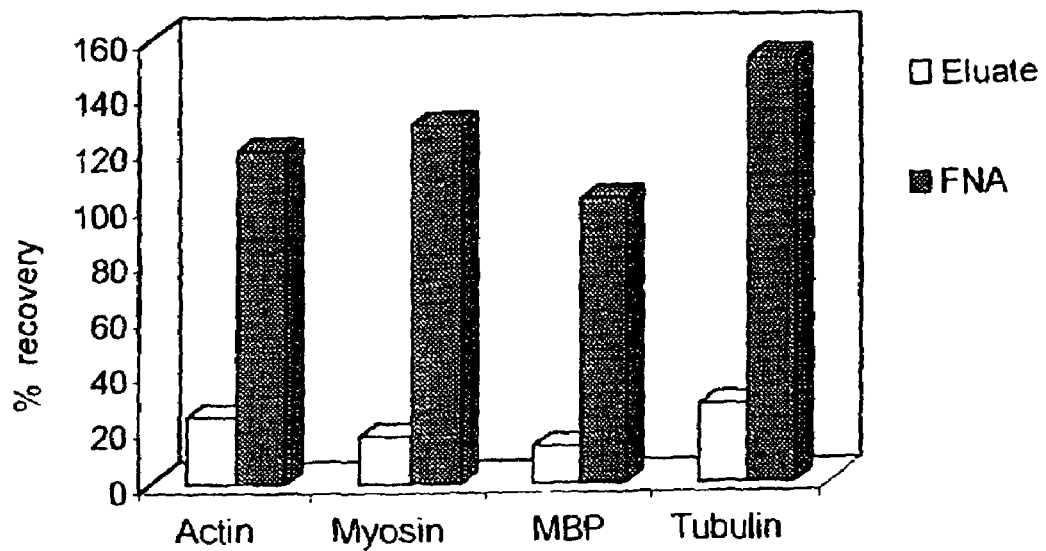

FIGS. 3A and 3C illustrate the specific reactivity with respect to IgG F(ab')2s and FIGS. 3B and 3D represent the reactivity with respect to autoantigens.

FIGS. 4A–4D: Evaluation of the properties of a fraction obtained using TEGELINE® (solid support based on NHS-Sepharose grafted with IgMs).

The parameters of the method for preparing this fraction are explained in greater detail in Example 4 hereinafter.

Figure 4A:
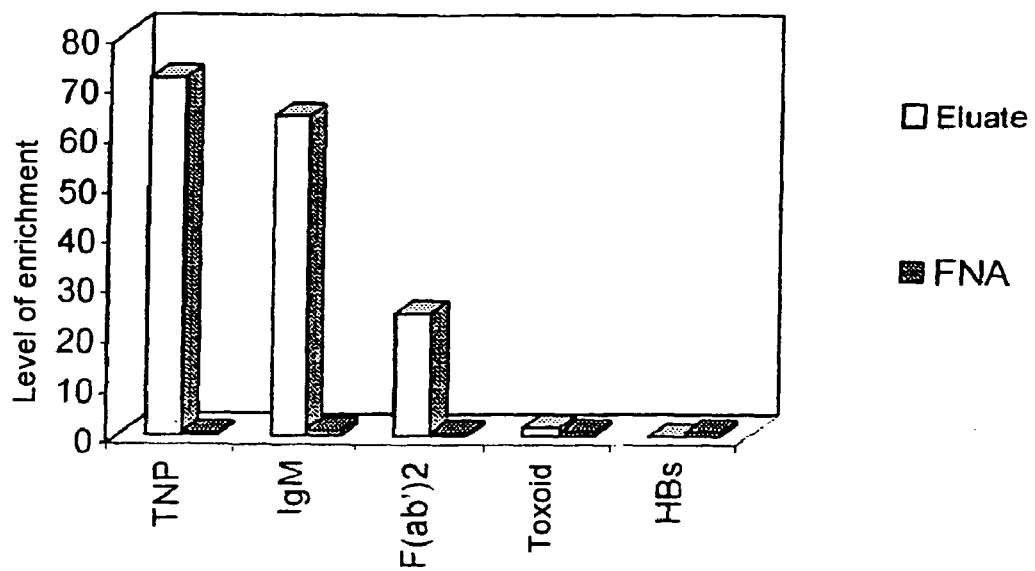
Figure 4B:
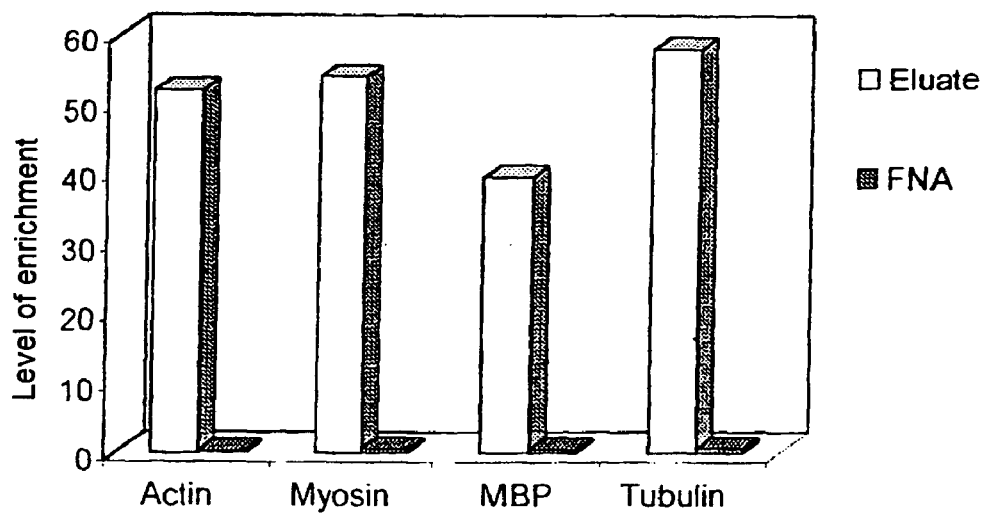
Figure 4C:
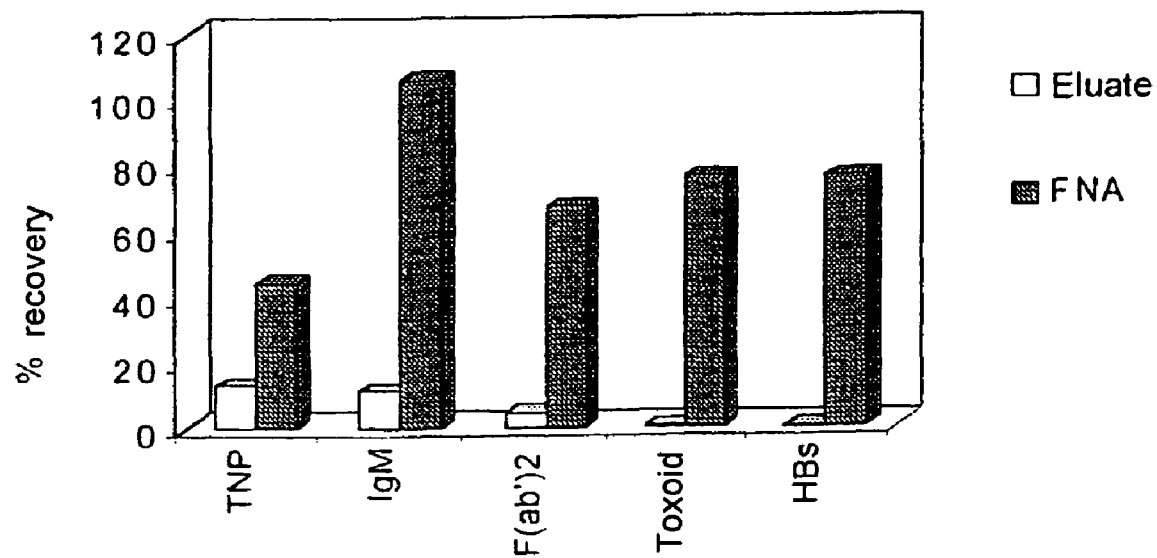
Figure 4D:
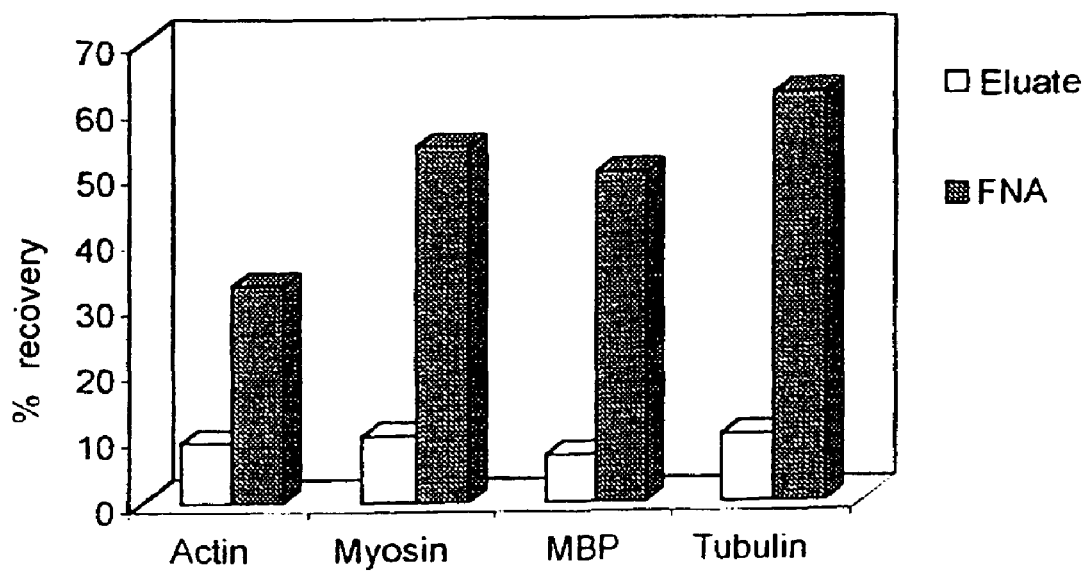

FIGS. 4A and 4C illustrate the specific reactivity with respect to IgMs and FIGS. 4B and 4D represent the reactivity with respect to autoantigens.

Figure 5:
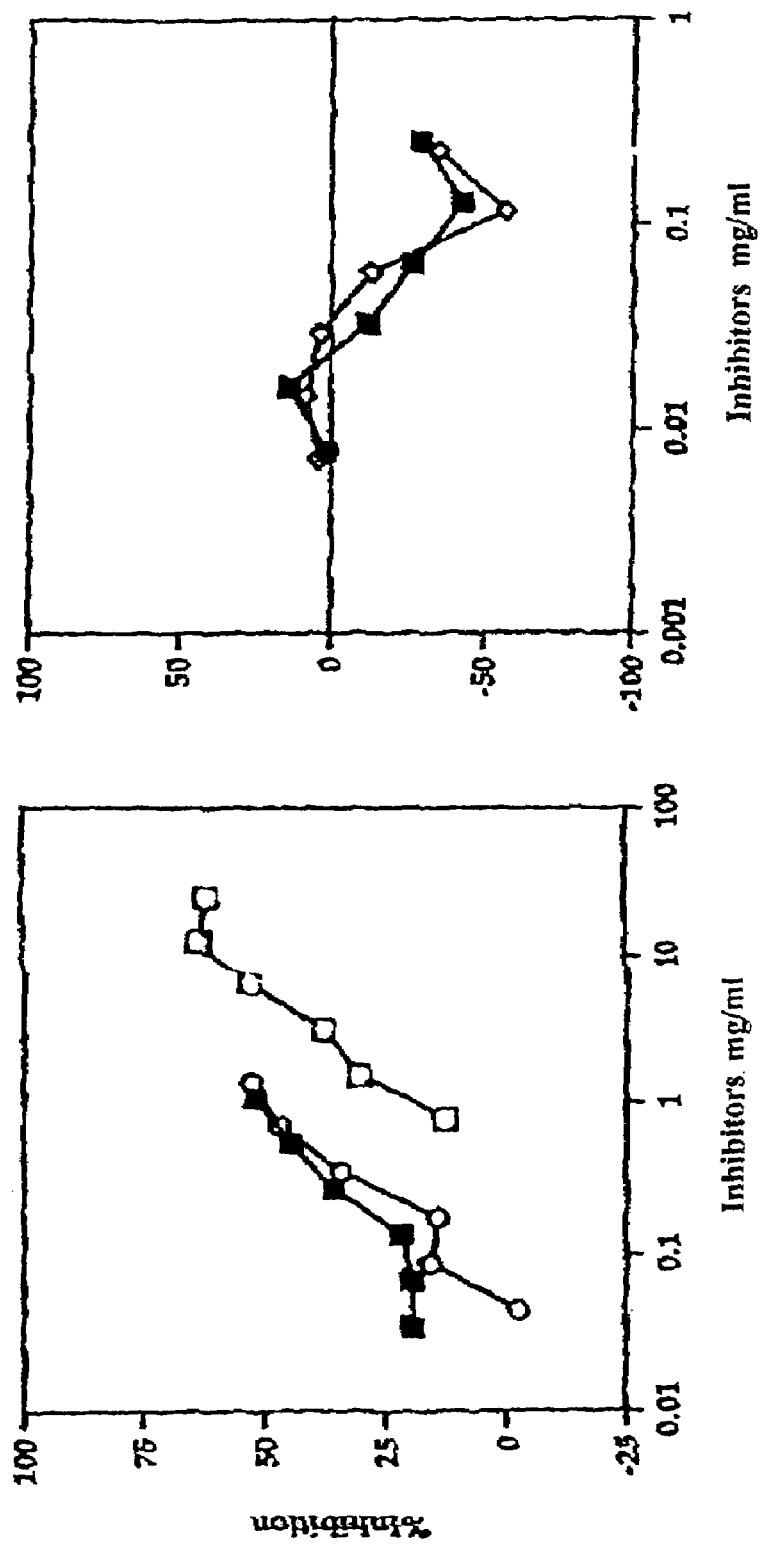

FIG. 5: Evaluation of the capacity of TEGELINE® or of the fractions to inhibit the binding between DNA and anti-DNA antibodies originating from a serum of a patient suffering from lupus erythematosis.

The experimental conditions of the competition assay are explained in example 6 hereinafter:
■ 47-2 EN (anti-DNP); ○ 47-4 EN (anti-DNP); □ Tegeline; ○ 46-8 EA (anti-Tegeline); ■ 46-9 EA (anti-Tegeline).

Figure 6:
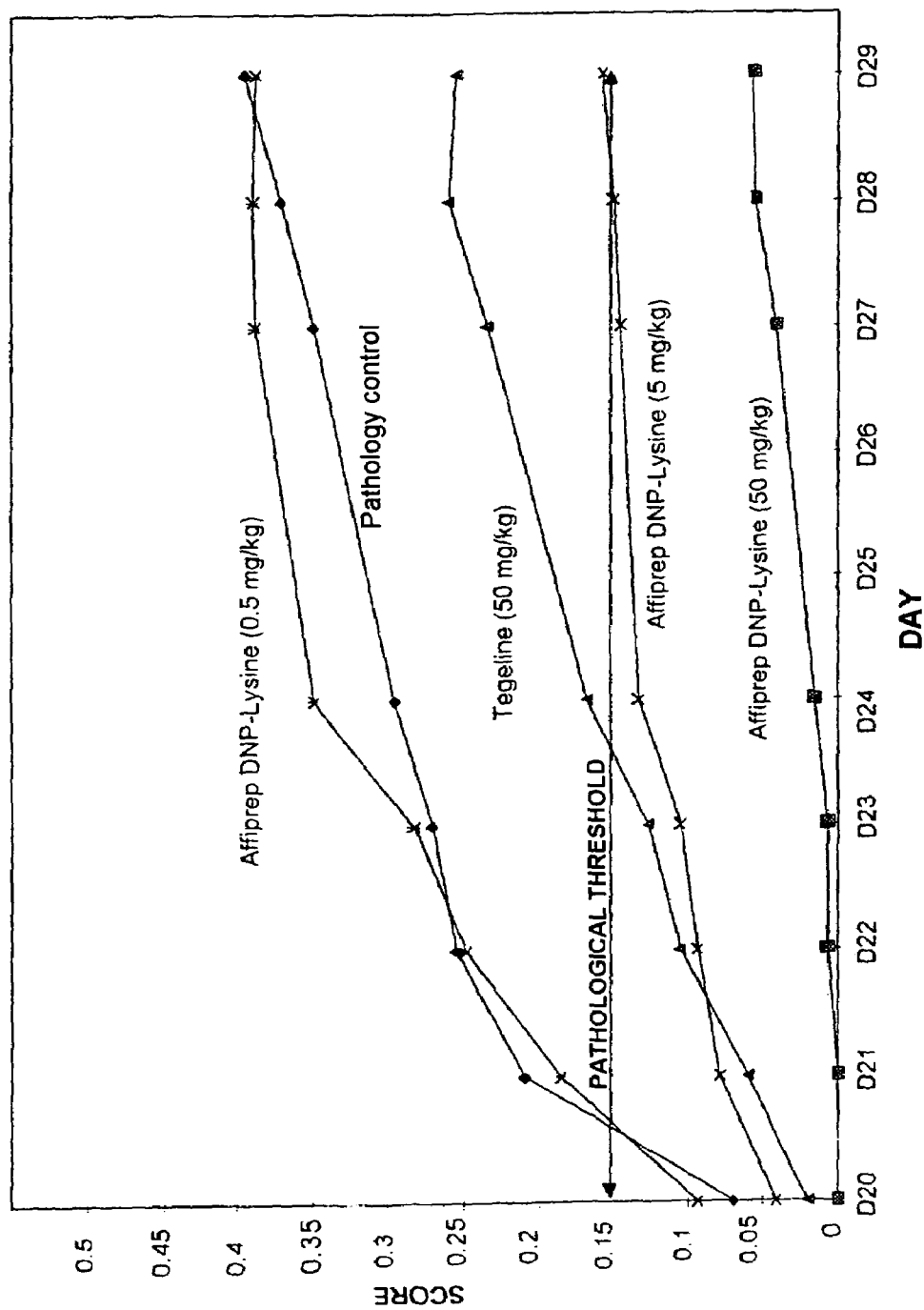

FIG. 6: Evaluation of the protective effect of the anti-DNP fraction compared to Tegeline on the development of rheumatoid arthritis induced in the rat by collagen II.

This figure represents the evolution of the arthritic score with DNP-LYSINE fractions.

The methods of induction of the disease and also of the administration of the products are described in example 7A hereinafter.

Figure 7:
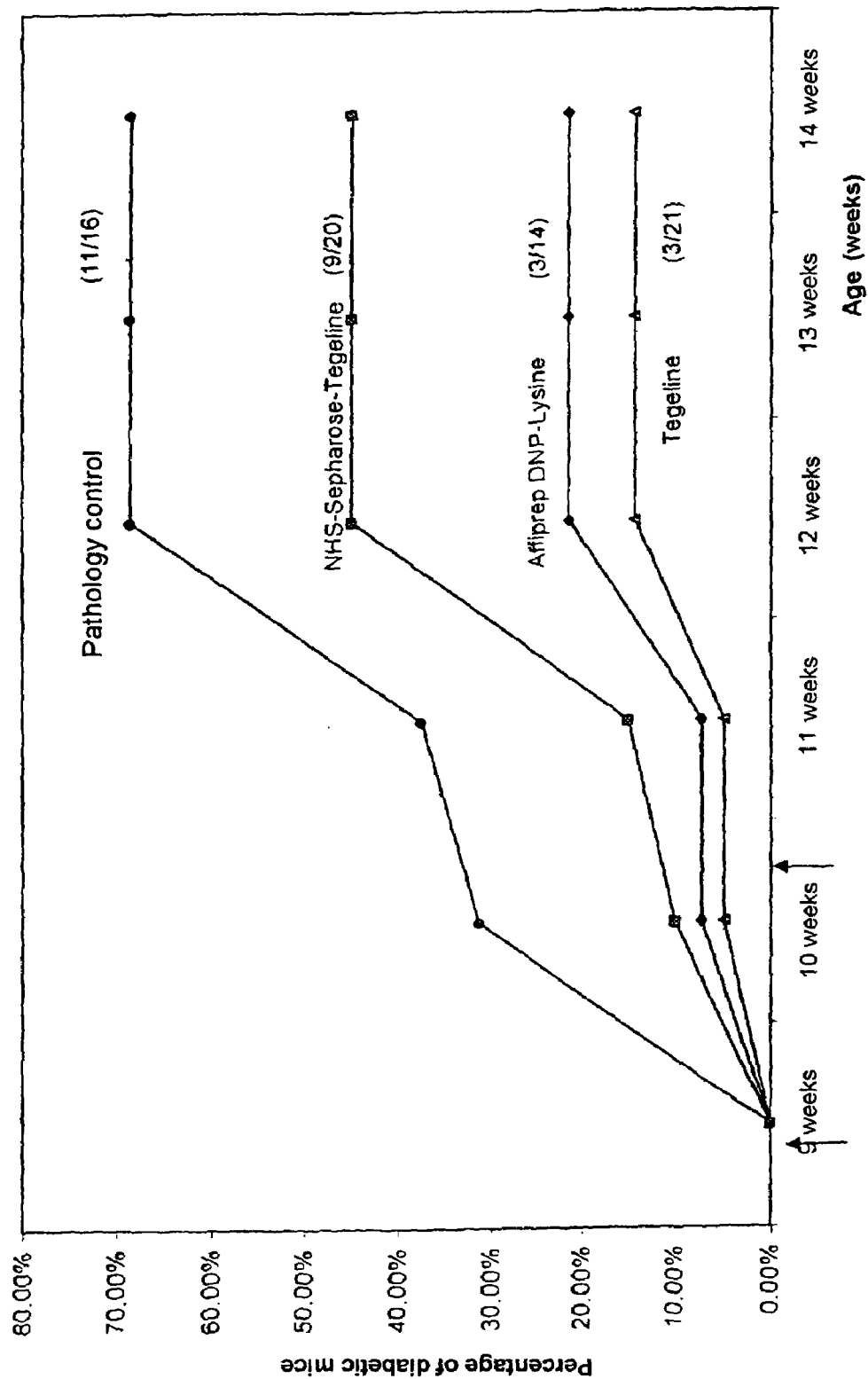

FIG. 7: Evaluation of the protective effect of the anti-DNP fraction compared to Tegeline on the development of diabetes induced by cyclophosphamide in male NOD mice.

The methods of induction of the disease and also of the administration of the products are described in example 7B hereinafter.

The methods for preparing and for evaluating the activity of fractions enriched in IgGs having the property of associating with other IgGs in interactions of the idiotypic type are given in greater detail in the examples hereinafter.

EXAMPLE 1

Method According to the Invention with TEGELINE® and an Affig 1 Solid Support

The polyvalent IgGs were coupled to a gel made of NHS-Affigel, in a proportion of 21 mg of product per ml of gel. A dose of 20 g of polyvalent IgGs at the concentration of 20 mg/ml was brought into contact, by column recirculation, with 2 l of immunoabsorbent for 4 h at 22° C. in PBS. The elution was then carried out in 0.1 M glycine-HCl, pH 3.25, and the eluate was concentrated on an ultrafiltration membrane with a cut-off threshold of 30 kD.

The concentration was measured by nephelometry. The recovery rate comes to 0.42% in the eluate and to 89% in the FNA.

The level of enrichment of reactivity with respect to F(ab')2s of this eluate compared to the starting poly-valent IgGs comes to 65.

This fraction has a reactivity which is enriched, compared to that of the polyvalent IgGs, with respect to several autoantigens and a lack of reactivity with respect to the tetanus toxoid and to the HBs antigen (see FIG. 1 and Table 1).

TABLE 1

| Antigens | Level of enrichment | | % recovery | |
|---|---|---|---|---|
| Tested | Eluate | FNA | Eluate | FNA |
| F(ab')2 | 65 | 0.3 | 28 | 26 |
| TNP | 90 | 0.7 | 39 | 62 |
| Toxoid | 1.8 | 1.1 | 0.8 | 106 |
| HBs | 2.5 | 1.4 | 1.1 | 132 |
| Actin | 63.5 | 0.7 | 27 | 69 |
| Myosin | 76 | 0.6 | 33 | 57 |
| MBP | 29 | 1 | 12 | 90 |
| Tubulin | 80 | 0.8 | 34 | 74 |

EXAMPLE 2

Method According to the Invention with TEGELINE® and an NHS-Sepharose Solid Support Polyvalent IgGs were coupled to a gel made of NHS-Sepharose, in a proportion of 10 mg of protein per ml of gel. A dose of 50 mg of polyvalent IgGs at the concentration of 1 mg/ml was brought into contact, by column recirculation, with 20 ml of immunoabsorbent for 4 h at 22° C. in PBS. The fraction not absorbed, or FNA, was collected and stored at −80° C. Elution was then carried out in 0.1 M glycine-HCl buffer, pH 3.5, and the eluate was concentrated by centrifugation on an ultrafiltration membrane with a cut-off threshold of 30 kD. The IgG concentration was measured by nephelometry. The recovery rate comes to 0.77% in the eluate and to 94.7% in the FNA.

The level of enrichment of reactivity with respect to F(ab')2s of this eluate compared to the starting poly-valent IgGs comes to 76.

This fraction has a reactivity which is enriched, compared to that of the polyvalent IgGs, with respect to several autoantigens and a lack of reactivity with respect to the tetanus toxoid and to the HBs antigen (see FIG. 2 and Table 2).

TABLE 2

| Antigens | Level of enrichment | | % recovery | |
|---|---|---|---|---|
| tested | Eluate | FNA | Eluate | FNA |
| TNP | 32 | 0.45 | 22 | 39 |
| F(ab')2 | 76 | 0.2 | 51 | 22 |
| Toxoid | 1.3 | 1 | 0.9 | 86 |
| HBs | 4.87 | 1.1 | 3.3 | 96.4 |
| Actin | 29.5 | 0.6 | 20 | 47 |
| Myosin | 35 | 0.6 | 24 | 55 |
| MBP | 29 | 0.7 | 20 | 58 |
| Tubulin | 22.4 | 0.6 | 15 | 54 |

EXAMPLE 3

Method According to the Invention with DNP-Lysine and an NHS-AffiPrep Support The DNP-Lysine was coupled to a gel made of NHS-Affiprep, in a proportion of 4 mg of product per ml of gel. A dose of 60 g of polyvalent IgGs at the concentration of 50 mg/ml was brought into contact, by column recirculation, with 2 l of immunoabsorbent for 4 h at 22° C. in PBS. The elution was then carried out in 2 M sodium iodide (KI) at pH 7. After concentrating on an ultrafiltration membrane with a cut-off threshold of 30 kD, the eluate is desalified against PBS on a Sephadex G 25 column.

The concentration was measured by nephelometry. The recovery rate comes to 0.12% in the eluate and to 85% in the FNA.

The level of enrichment of reactivity with respect to TNP-Ova of this eluate compared to the starting polyvalent IgGs comes to 239.

This fraction has a reactivity which is enriched, compared to that of the polyvalent IgGs, with respect to several autoantigens and a lack of reactivity with respect to the tetanus toxoid and to the HBs antigen (see FIG. 3 and Table 3).

TABLE 3

| Antigens | Level of enrichment | | % recovery | |
|---|---|---|---|---|
| Tested | Eluate | FNA | Eluate | FNA |
| TNP | 239 | 0.9 | 23 | 94 |
| F(ab')2 | 2.9 | 0.9 | 0.6 | 92 |
| Toxoid | 2.4 | 1 | 0.5 | 104 |
| HBs | 3.2 | 1 | 0.7 | 104 |
| Actin | 117 | 1.1 | 24 | 120 |
| Myosin | 83 | 1.2 | 17 | 129 |
| MBP | 63 | 1 | 13 | 102 |
| Tubulin | 137 | 1.5 | 28 | 152 |

EXAMPLE 4

Method According to the Invention with Polyclonal IgMs and an NHS-Sepharose Solid Support Human polyclonal IgMs (purity 90%) were coupled to a gel made of NHS-Sepharose, in a proportion of 10 mg of proteins per ml of gel. A dose of 50 mg of polyvalent IgGs at the concentration of 1 mg/ml was brought into contact with 20 ml of immunoadsorbent for 4 h at 22° C. in PBS. The fraction not adsorbed, or FNA, was collected and stored at −80° C. The elution was then carried out in 0.1 M glycine-HCL buffer, pH 3.5, and the eluate was concentrated by centrifugation on an ultrafiltration membrane with a cut-off threshold of 30 kDa.

The IgG concentration was measured by nephelometry. The recovery rate comes to 0.20% in the eluate and to 98.7% in the FNA.

The level of enrichment of reactivity with respect to IgMs of this eluate compared to the starting polyvalent IgGs comes to 64.

This fraction has a reactivity which is enriched, compared to that of the polyvalent IgGs, with respect to several autoantigens and a lack of reactivity with respect to the tetanus toxoid and to the HBs antigen (see FIG. 4 and Table 4).

TABLE 4

| Antigens | Level of enrichment | | % recovery | |
|---|---|---|---|---|
| tested | Eluate | FNA | Eluate | FNA |
| TNP | 71.5 | 0.5 | 13 | 44.5 |
| IgM | 64 | 1.2 | 11.4 | 106 |
| F(ab')2 | 24.5 | 0.7 | 4.5 | 67 |
| Toxoid | 1.8 | 0.8 | 0.3 | 76 |
| HBs | <threshold | 0.8 | <threshold | 76 |
| Actin | 52 | 0.3 | 9 | 33 |
| Myosin | 54 | 0.6 | 10 | 54 |
| MBP | 39.5 | 0.5 | 7 | 50 |
| Tubulin | 58 | 0.7 | 10 | 62 |

EXAMPLE 5

Inhibition of the Proliferation of Human Lymphocytes in MLC

The lymphocytes from a donor A and from a donor B which are incompatible in terms of the HLA molecules were separated on ficoll and cultured at the concentration of $2 \times 10^5$ per well in PPMI 1640 medium supplemented with 10% of fetal calf serum. Decrease in concentrations of Tegeline, of Fc or F(ab')2 fragments of Tegeline or of the various fractions given in examples 1 to 4 are added to the medium. After culturing for 4 days at 37° C. in a $CO_2$ atmosphere, 1 μCi=37 KBq of tritiated thymidine is added for the last 6 h of culturing. The amount of incorporation of tritiated thymidine into the human cells, which reflects the proliferation, is measured using a β scintillation counter. The percentage inhibition of the proliferation of the lymphocytes in the presence of the various components added to the culture is calculated relative to the proliferation of the mixed donor A and donor B cells. Table 5 gives the results in terms of dose in μg/ml of fractions or of products capable of giving 50% inhibition of the proliferation of the cells. The fractions given in examples 1 to 4 are capable of inhibiting the proliferation of the lymphocytes in mixed culture with an effectiveness 10 to 50 times greater than that of Tegeline.

TABLE 5

Inhibition by TEGELINE ® and by the fractions of the proliferation of human lymphocytes in mixed culture

| Reference fractions | Affinity support | Dose in μg/ml giving 50% inhibition of the proliferation | |
|---|---|---|---|
| | | Experiment 1 | Experiment 2 |
| Tegeline ® | NA | 160 | 80 |
| Fc of Tegeline ® | NA | 1000 | NT |
| F(ab')2 of Tegeline ® | NA | NT | 250 |
| Example 1 | AffiGel NHS Tegeline | 7 | NT |
| Example 2 | Sepharose NHS Tegeline | 5 | NT |
| Example 3 | AffiPrep NHS DNP-Lysine | 9 | 2 |
| Example 4 | Sepharose NHS IgM | 2.5 | — |

NA = not applicable
NT = not tested

EXAMPLE 6

Competition Assay for the Fractions with Respect to Pathogenic Antibodies

Tegeline or the anti-Tegeline fractions prepared according to example 2 or the anti-DNP fractions prepared according to example 3 are incubated, in the presence of biotinylated anti-DNA antibodies originating from a patient suffering from lupus erythematosus, in a microfiltration plate coated with DNA. The percentage inhibition of the binding of the biotinylated anti-DNA antibodies to the DNA is measured as a function of the concentration of Tegeline or of the fractions added. The results given in FIG. 5 show that the anti-DNP fractions inhibit the proliferation approximately ten times more than Tegiline for the same concentration. The anti-Tegeline fractions, on the other hand, promote the binding of the pathogenic antibodies to the DNA by establishing interactions of the idiotypic type.

EXAMPLE 7

Clinical Applications

The fractions which are enriched in autoreactivity and which show themselves to be effective in the experimental models of autoimmune diseases are intended to be used in the treatment of many pathological conditions in which IVIgs have been shown to a have a therapeutic action, and in particular autoimmune diseases, GVH and graft rejection after trans-plantation.

EXAMPLE 7A

Effect of the anti-DNP fractions compared to Tegeline on the development of rheumatoid arthritis induced in the rat by collagen II.

The fractions enriched in autoreactivity which originate from the elution of polyvalent IgGs from a gel made of NHS-Affiprep coupled to DNP-Lysine (FIG. 3 and example 3) were injected ip at various doses into rats which had been given collagen II to induce the development of rheumatoid arthritis. The effectiveness of protection against rheumatoid arthritis of the fractions was compared to that obtained with the same doses of initial polyvalent IgGs. The cumulated results of two independent experiments (FIG. 6) show that the dose effective on the development of rheumatoid arthritis of the fractions originating from the elution of the gel made of NHS-Affiprep coupled to DNP-Lysine is ten times less than the effective dose of Tegeline.

EXAMPLE 7B

Effect of the anti-Tegeline fraction and of the anti-DNP fraction on the development of diabetes induced by cyclophosphamide in male NOD mice.

Newborn male NOD mice are injected three times a week for four weeks either with Tegeline at the dose of 1 mg/young mouse, or with the anti-Tegeline fraction or anti-DNP fraction at the dose of 0.1 mg/young mouse. The development of diabetes is triggered at 8 weeks old by two injections of cyclophosphamide (200 mg/kg) two weeks apart. FIG. 7 shows that the percentage of diabetic mice (level of sugar in blood greater than 3 g/l) is significantly decreased in the group of NOD mice injected with Tegeline (14%) and in the group injected with the anti-DNP fraction (21%), but not in the group injected with the anti-Tegeline fraction, compared to the nontreated group (68%).

These indications are not exclusive and may be extended. Said fractions are formulated with a pharmaceutical vehicle suitable for intravenous administration, with packaging either in lyophilized form or in liquid form, or another route (IP, ID, IM), depending on the desired indications.

REFERENCES

1. Imbach P., Barandum S., D'Apuzzo V., Baumgartner C., Hirt A., Morell A., Rossi E., Schoni M., Vert-Wagner. High dose intravenous gammaglobulin for idiopathic thrombocytopenic purpura in childhood. The Lancet, 1981, i: 1128–1231.
2. Furusho K. et al. High-dose intravenous gammaglobulin for Kawaski disease. The Lancet, 1984; 1055–1058.
3. Newburger J. W. et al. A single intravenous infusion of gammaglobulin as compared with four infusions in the treatment of acute Kawasaki syndrome. N. Engl. J. Med, 1991; 324: 1633–1639.
4. Sullivan K. M. Immunomodulation in allogenic marrow transplantation: use of intravenous immune globulin to suppress acute graft-versus-host disease. Clin. Exp. Immunol., 1996, 104 (suppl. 1): 43–48.
5. Saoudi A., Hurez V., de Kozak Y., Kuhn J., Kaveri S. V., Kazatchkine M. D. et al. Human immunoglobulin preparations of intravenous use prevent experimental autoimmune uveoretinis. Int. Immunol., 1993; 5(12): 1559–1597.
6. Björkholm M. Intravenous immunoglobulin treatment in cytopenic haematological disorders J. Int. Med. 1993; 234: 119–126
7. Sultan Y., Kazatchkine M.D., Maisonneuve P., Nydegger U. Anti-idiotypic suppression of auto-antibodies to factor VIII (anti-haemophilic factor) by high-dose intravenous gammaglobulin. Lancet, 1984; 2: 765–768.
8. Schwartz R. S., Gabriel D. A., Aledort L. M., Green D. and Kessler C. M. A prospective study of treatment of acquired (autoimmune) factor VIII inhibitors with high-dose intravenous gammaglobulin. Blood, 1995; 86 (2): 797–804.
9. Coulam C. B., Krysa L., Strern J. J. and Bustillo M. Intravenous immunoglobulin for treatment of recurrent pregnancy loss. American Journal of Reproductive Immunology, 1995; 34: 333–337.
10. Raziel A., Herman A., Bukovsky I., Caspin E. and Ronel R. Intravenous immunoglobin treatment of pregnant patients with unexplained recurrent abortions. Human reproduction, 1996; 11(4): 711–715.
11. Van der Meché F.G.A., Schmitz P.I.M. and the dutch Guillain-Barré study group. A randomized trial comparing intravenous immune globulin and plasma exchange in Guillain-Barré syndrome. N. Engl. J. Med, 1992; 326: 1123–1129.
12. Plasma exchange/Sandoglobulin Guillain-Barrée syndrome trial group. Randomised trial of plasma exchange, intravenous immunoglobulin and combined treatments in Guillain-Barrée syndrome. Lancet, 1997; 349: 225–230.
13. Abdallah S. A., Jansen P. W., Ashwal S., Perkin R. M. Intravenous immunoglobulin as therapy for pediatric Guillain-Barrée syndrome. J. Child. Neurol, 1997; 12: 376–380.
14. Hahn A. F., Bolton C. F., Zochodne D. and Feasby T. E. Intravenous immunoglobulin treatment in chronic inflammatory demyelinating polyneuropathy. A double blind, placebo controlled, cross-over study. Brain, 1996; 119: 1067–1077.
15. Dalakas M. C., Illa I., Dambrosia J. M., Soueidan S. A., Stein D. P., Otero C. et al. A controlled trial of high-dose intravenous immune globulin infusions as treatment of dermatomyositis. N. Engl. J. Med, 1993; 329: 1993–2000.
16. Gajdos P., Chevret S., Clair B., Tranchant C., Chastang C. Clinical trial of plasma exchange and high-dose intravenous immunoglobulin in myasthenia gravis. Ann. Neurol, 1997; 41: 789–796.
17. Fazekas F., Deisenhammer F., Stasser-Fuchs S., Nahler G. and Mamoli B. Randomised placebo controlled trial of monthly intravenous immunoglobulin therapy in relapsing remitting multiple sclerosis. Lancet, 1997, 349: 589–593.
18. Mouthon L., Kaveri S. V., Spalter S. H., Lacroix-Desmazes S., Lefranc C., Desai R., Kazatchkine M.D. Mechanisms of action of intravenous immunoglobulin in immune-mediated diseases. Clin. Exp. Immunol, 1996; 104 (suppl. 1): 3–9.
19. Kaveri S., Dietrich G., Kazatchkine M. Can intravenous immunoglobulin treatment regulate autoimmune responses. Seminars in Hematol., 1992; 29: 64.
20. Ronda N., Haury M., Nobrega A., Coutinho A., Kazatchkine M. Selectivity of recognition of variable (V) regions of autoantibodies by intravenous immunoglobulin (IVIg). Clin. Immunol. Immunopathol., 1994; 70: 124.
21. Hurez V., Kaveri S. V. and Kazatchkine M.D., Expression and control of the natural autoreactive IgG repertoire in normal human serum. Eur. J. Immunol. 1993. 23: 783–789.
22. Rossi F., Kazatchkine M. Anti-iodiotype against autoantibodies in pooled normal human polyspecific Ig. J. Immunol., 1989; 143: 4104.
23. Hurez V., Kazatchkine M.D., Vassilev T., Ramanathan S., Pashov A., Basuyaux B, De Kosak Y., Bellon B., Kaveri S. V. Pooled normal human polyspecific IgM contains neutralizing anti-idiotypes to IgG autoantibodies of autoimmune patients and protects from experimental autoimmune disease. Blood, 1997; 90: 001.
24. Berneman A., Guilbert B., Eschrich S. and Avrameas S. IgG auto- and polyreactives of normal human sera. Molecular Immunol., 1993; 30: 1499–1510.

What is claimed is:

1. An Ig fraction obtained by a method comprising
a) preparing an insoluble support onto which is grafted a component selected from the group consisting of polyvalent IgGs, polyvalent IgMs and DNP-lysine,
b) adsorbing polyvalent Igs onto the support obtained in step a),
c) eluting the Igs retained on a portion of immunoglobulins bound to the support, so as to collect a first intermediate fraction connected through IgG-IgG or IgM-IgG idiotypic interactions, or eluting a second intermediate fraction which interacts with DNP,
d) selecting from the first or the second intermediate fraction a third intermediate fraction having reactivity with IgMs, IgG F(ab')2s or DNP, little or no reactivity with non-self antigens and/or polyreactivity with autoantigens, and
e) selecting from the third intermediate fraction the Ig fraction having activity which inhibits a proliferation of lymphocytes in mixed culture.

2. The Ig fraction of claim 1, wherein the Ig fraction inhibits the proliferation of lymphocytes 10 to 50 times more effectively than commercially available, polyvalent IgGs.

3. The Ig fraction of claim 1, wherein the Ig fraction contains the polyvalent Igs selected from the group consisting of IgGs and IgMs.

4. A method of treating an autoimmune disease in a patient comprising administering to said patient an effective amount of the IG fraction of claim 1.

5. A method of treating graft-versus-host-disease in a patient comprising administering to said patient an effective amount of the Ig fraction of claim 1.

6. A method of preventing or treating graft rejection after transplantation in a patient comprising administering to said patient an effective amount of the composition of claim 1.

7. A method of treating in a patient a neurological disease selected from the group consisting of adult Guillain-Barre syndrome chronic demyelinating inflammatory polyneuropathies, dermatomyositis, myasthenia and multiple sclerosis comprising administering to said patient an effective amount of the Ig fraction of claim 1.

8. A method for preparing an Ig fraction comprising
a) preparing an insoluble support onto which is grafted a component selected from the group consisting of polyvalent IgGs, polyvalent IgMs and DNP-lysine,
b) adsorbing polyvalent Igs onto the support obtained in step a),
c) eluting the Igs retained on a portion of immunoglobulins bound to the support, so as to collect a first intermediate fraction connected through IgG-IgG or IgM-IgG idiotypic interactions, or eluting a second intermediate fraction which interacts with DNP,
d) selecting from the first or the second intermediate fraction a third intermediate fraction having reactivity with IgMs, IgG F(ab')2s or DNP, little or no reactivity with non-self antigens and/or polyreactivity with autoantigens, and
e) selecting from the third intermediate fraction the Ig fraction having activity which inhibits a proliferation of lymphocytes in mixed culture.

9. The method of claim 8, wherein the polyvalent Igs consist of IgGs or IgMs.

10. The method of claim 8, wherein step d) further comprises measuring a level of enrichment of antibodies reactive against IgMs, IgG F(ab')2s or a hapten DNP used for purification.

11. The method of claim 8, wherein step d) comprises an ELISA carried out on a panel of autoantigens selected from the group consisting of actin, myosin, MBP and tubulin.

12. The method of claim 8, wherein the Igs absorbed in step b) are eluted with a buffer comprising a chaotrope selected from the group consisting of glycine-HCl and sodium iodide.

13. The method of claim 8, wherein the adsorbing step is carried out in phosphate buffered saline under temperature conditions ranging from 4° to 40° C.

* * * * *